United States Patent [19]

Haber

[11] Patent Number: 4,820,827

[45] Date of Patent: Apr. 11, 1989

[54] 2,3-DIARYL-5-BROMOTHIOPHENE COMPOUNDS OF USE FOR THE TREATMENT OF INFLAMMATON AND DYSMENORRHEA

[75] Inventor: Stephen B. Haber, Wilmington, Del.

[73] Assignee: E. I. Du Pont de Nemours and Company, Wilmington, Del.

[21] Appl. No.: 577,650

[22] Filed: Feb. 10, 1984

Related U.S. Application Data

[63] Continuation-in-part of Ser. No. 570,450, Jan. 17, 1984, Pat. No. 4,590,205, which is a continuation of Ser. No. 354,300, Mar. 3, 1982, abandoned.

[51] Int. Cl.$^4$ .................. C07D 333/16; C07D 333/08
[52] U.S. Cl. ......................................... 549/78; 549/80
[58] Field of Search ............................. 549/80, 62, 78

[56] References Cited

U.S. PATENT DOCUMENTS

| | | | |
|---|---|---|---|
| 2,625,553 | 1/1953 | Pines et al. | 260/332.5 |
| 2,639,286 | 5/1953 | Mavity | 260/329 |
| 4,174,405 | 11/1979 | Relyea et al. | 424/275 |
| 4,302,461 | 11/1981 | Cherkofsky | 549/62 |
| 4,381,311 | 4/1983 | Haber . | |

*Primary Examiner*—Alan Siegel

[57] ABSTRACT

A small group of 2,3-diaryl-5-bromothiophene compounds such as 5-bromo-2-(4-methylthiophenyl)-3-(4-fluorophenyl)thiophene have been found to possess significant and unexpected antiinflammatory activity, and inhibition of prostaglandin synthetase useful for the treatment of arthritis and dysmenorrhea.

5 Claims, No Drawings

2,3-DIARYL-5-BROMOTHIOPHENE COMPOUNDS OF USE FOR THE TREATMENT OF INFLAMMATON AND DYSMENORRHEA

RELATED APPLICATIONS

This application is a continuation-in-part of application U.S. Ser. No. 570,450 now U.S. Pat. No. 4,590,205, filed Jan. 17, 1984, which in turn is a continuation application of my application U.S. Ser. No. 354,300, filed Mar. 3, 1982, now abandoned.

TECHNICAL FIELD

This invention relates to four 2,3-diaryl-5-bromothiophene compounds which unexpectedly possess antiinflammatory and prostaglandin synthetase inhibitory activity useful for the treatment of arthritis and dysmenorrhea.

BACKGROUND OF THE INVENTION

Compounds of this general type are known in the art, but not as antiinflammatory agents or as agents to treat dysmenorrhea. A number of references including J. L. Melles and H. J. Backer, *Rec. trav. chim.*, Vol. 72, 314 (1953), and S. Hauptmann and E. -M. Werner, *J. prakt. Chem.*, Vol. 314, 499 (1972), disclose the preparation of 2,3-diphenylthiophene.

Melles and Backer, op. cit., describe the preparation of 2-bromo-3,4-diphenylthiophene; 4,5-dibromo-2,3-diphenylthiophene; 3,5-dibromo-2,4-diphenylthiophene; and 3,4-dibromo-2,5-diphenylthiophene. U.S. Pat. No. 4,174,405 describes 2-halo-3,5-diarylthiophenes and their use as acaricides.

U.S. Pat. No. 4,302,461 issued to Cherkofsky on Nov. 24, 1981, generically and broadly discloses compounds of the formula

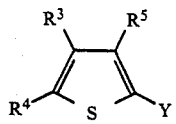

where Y can be either H or Br, as members of a reaction sequence to produce alkylthio substituted thiophenes useful as antiinflammatory agents. No intrinsic utility or biological activity is disclosed for the compounds pictured above.

In addition, the synthesis of the preferred 2-trifluoromethylthio and 2-trifluoromethylsulfonyl substituted compounds of the U.S. Pat. No. 4,302,461 patent utilizes trifluoromethanesulfenyl chloride which is extremely toxic [Chemical & Engineering News, Vol. 45, 44 (1967)]. In contrast, the compounds of the instant invention are made utilizing relatively non-toxic bromine as a reagent.

U.S. patent application Ser. No. 354,300 filed Mar. 3, 1982, by Haber discloses compounds of the formula,

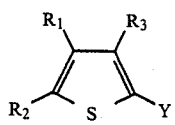

where Y can be F, Cl, Br, or I, but does not claim any composition of matter containing bromine. Three of the four compounds claimed in the instant application are disclosed on page 4 of U.S. Ser. No. 354,300 as specifically preferred in view of their outstanding activity.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited, however, because of toxicity and adverse side-effects. Many produce gastric irritation and other effects, such as changes in blood cells and in the central nervous system. Adrenocortical steroids produce gastric irritation and suppression of normal adrenal function.

Dysmenorrhea is a painful condition associated with menstruation which affects an estimated 30–50 percent of women of childbearing age causing the loss of more than 140 million working hours per year [J. L. Marx, Science, Vol. 205, 175 (1979)]. The symptoms of dysmenorrhea include nausea, vomiting, diarrhea, and headache. Abnormally high levels of prostaglandin compounds occur in the endometrium and menstrual fluid of patients suffering from primary dysmenorrhea. Prostaglandins are known to cause uterine contractions, sensitize nerve endings to pain, and cause the typical symptoms of the condition. Treatment of dysmenorrhea with prostaglandin synthetase inhibitors reduces prostaglandin levels and relieves the symptoms of dysmenorrhea [M. R. Henzl and A. Izu, *Acta. Obstet. Gynecol. Scand. Suppl.*, Vol. 87, 105–117 (1979) and W. Y. Chan, M. Y. Dawood, and F. Fuchs, *Am. J. Obstet. Gynecol.*, Vol. 135, 102–108 (1979)].

There is thus a clear need for improved antiinflammatory agents, especially ones which also possess activity as prostaglandin synthetase inhibitors which would be independently useful for treatment of dysmenorrhea.

SUMMARY OF THE INVENTION

The unexpected finding that the four (4) compounds comprising the instant invention possess antiinflammatory activity and prostaglandin synthetase inhibition activity is of major significance. Specifically, this invention relates to compounds of Formula I:

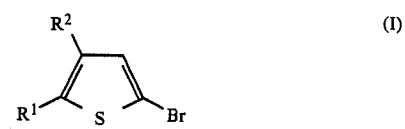

wherein
$R^1$ is 4-fluorophenyl, 4-methylthiophenyl, or 4-methylsulfonylphenyl; and
$R^2$ is 4-fluorophenyl, 4-methylthiophenyl, or 4-methylsulfonylphenyl;
with the proviso that there must be one, and only one, 4-fluorophenyl substituent selected for $R^1$ and $R^2$.

DETAILED DESCRIPTION

Synthesis

The compounds of the invention are prepared by the following general reaction scheme.

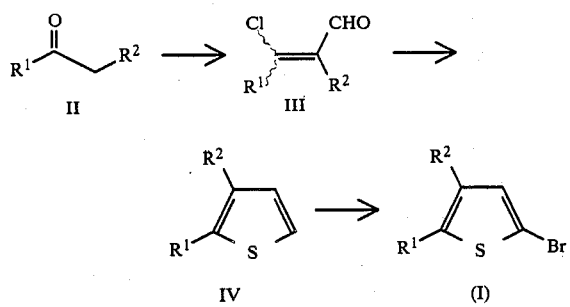

A desoxybenzoin II is reacted with the Vilsmeier reagent (dimethylformamide/phosphorus oxychloride) to give chloro aldehyde III. Similar reactions are described in M. Weissenfels et al., Z. Chem., 6, 471-2 (1966). Reaction of III with mercaptoacetic acid in pyridine in the presence of triethylamine gives thiophene IV. This is analogous to a procedure described in N. D. Trieu and S. Hauptmann, Z. Chem., 13, 57-8 (1973). 2-Bromo-4,5-diarylthiophenes are then prepared by reaction of IV with bromine in methylene chloride, acetic acid, or their mixture at temperatures from about −20° to about 30° C. When one of $R^1$ and $R^2$ is 4-methylthiophenyl, oxidation with an oxidizing agent such as m-chloroperoxybenzoic acid gives the corresponding 4-methylsulfonylphenyl analog.

4-Fluorobenzyl 4-methylthiophenyl ketone (II; $R^1=4-CH_3SC_6H_4$, $R^2=4-FC_6H_4$), the starting material for compounds of this invention where $R^1=4$-methylthiophenyl or 4-methylsulfonylphenyl, is conveniently prepared by the Friedel-Crafts reaction of 4-fluorophenylacetyl chloride and thioanisole in the presence of a Lewis acid such as aluminum chloride in a solvent such as methylene chloride at temperatures from about −10° to about 30°. 4-Fluorophenyl 4-methylthiobenzyl ketone (II; $R^1=4-FC_6H_4$, $R^2=4-CH_3SC_6H_4$), the starting material for compounds of this invention where $R^2=4$-methylthiophenyl or 4-methylsulfonylphenyl, may be prepared according to the procedure of Bender et al., U.S. Pat. No. 4,153,706.

The compounds of the invention and their synthesis are further illustrated by the following examples. All temperatures are in degrees Centigrade.

EXAMPLE 1

5-Bromo-3-(4-fluorophenyl)-2-(4-methylthiophenyl)thiophene

A solution of 3-(4-fluorophenyl)-2-(4-methylthiophenyl)thiophene (15 g, 50 mmole) in methylene chloride (150 ml) was diluted with 150 ml of acetic acid and cooled to about 5°. A 1M solution of bromine in acetic acid (55 ml, 1.1 equiv.) was then added dropwise. The reaction mixture was stirred at 0° for 1.5 hours and then concentrated in vacuo. The residue was dissolved in ethyl acetate and the solution washed with saturated aqueous sodium bicarbonate and brine, dried, and concentrated in vacuo. Recrystallization from ethanol gave the title compound (15.4 g), m.p. 113°–116°.

NMR spectral data of the product of a similar preparation were consistent with the assigned structure.

MS: m/z 378 and 380 (M+), 363 and 365 (M—$CH_3$).

EXAMPLE 2

5-Bromo-2-(4-fluorophenyl)-3-(4-methylsulfonylphenyl)thiophene a.

2-(4-Fluorophenyl)-3-(4-methylsulfonylphenyl)thiophene

A solution 2-(4-fluorophenyl)-3-(4-methylthiophenyl)thiophene (9 g, 30 mmole) in methylene chloride (100 ml) was treated with a solution of m-chloroperoxybenzoic acid (MCPBA; 80%; 14.3 g, 66 mmole) in 200 ml of methylene chloride and then heated at reflux for 1 hour. The reaction mixture was cooled in an ice bath and filtered. The filtrate was washed with saturated aqueous sodium bicarbonate and brine, dried, and evaporated to give the title compound. The NMR spectrum, which was consistent with the assigned structure, indicated that the sample still contained $CH_2Cl_2$.

MS: m/z 332 (M+).

b.

5-Bromo-2-(4-fluorophenyl)-3-(4-methylsulfonylphenyl)thiophene

A solution of the crude 2-(4-fluorophenyl)-3-(4-methylsulfonylphenyl)thiophene of Example 2a (12.6 g, up to 30 mmole) in methylene chloride (100 ml) was diluted with 75 ml of acetic acid and cooled to about 5°. A 1M solution of bromine in acetic acid (33 ml, 1.1 equiv) was added and the reaction stirred at about 5°. After 1 hour, additional bromine solution (5 ml) was added. After 2 hours total reaction time, the reaction mixture was concentrated in vacuo. The residue was dissolved in ethyl acetate and the solution washed with saturated aqueous sodium bicarbonate and brine, dried, and concentrated in vacuo. Recrystallization from ethanol gave the title compound (7.9 g), m.p. 122°–124°. Infrared and NMR spectral data were consistent with the assigned structure.

MS: m/z 410 and 412 (M+), 331 and 333 (M—$CH_3SO_2$).

EXAMPLE 3

5-Bromo-2-(4-fluorophenyl)-3-(4-methylthiophenyl)thiophene

A solution of 2-(4-fluorophenyl)-3-(4-methylthiophenyl)thiophene (7.5 g, 25 mmole) in methylene chloride (75 ml) was diluted with 75 ml of acetic acid, cooled to about 5°, and treated dropwise with a 1M solution of bromine in acetic acid (28 ml, 1.1 equiv). The reaction mixture was stirred at 5° for 1.5 hours and then concentrated in vacuo. The residue was dissolved in ethyl acetate and the solution washed with saturated aqueous sodium bicarbonate and brine, dried, and evaporated. Recrystallization from methanol, with cooling in Dry Ice, gave the title compound in two crops (7.60 g), m.p. 75°–78°. Infrared and NMR spectral data were consistent with the assigned structure.

MS: m/z 378 and 380 (M+), 363 and 365 (M—$CH_3$).

EXAMPLE 4

5-Bromo-3-(4-fluorophenyl)-2-(4-methylsulfonylphenyl)thiophene a. 3-(4-Fluorophenyl)-2-(4-methylsulfonyl)thiophene A solution of 3-(4-fluorophenyl)-2-(4-methylthiophenyl)thiophene (600 mg, 2 mmole) in methylene chloride (6 ml) was treated with a solution of MCPBA (475 mg, 2.2 mmole) in 8 ml of methylene chloride and the resulting mixture heated to reflux. After 1 hour, an additional portion of MCPBA (475 mg, 2.2 mmole) in 6 ml of methylene chloride was added; heating was continued overnight. The reaction mixture was cooled in an ice bath and filtered. The filtrate was washed with saturated aqueous sodium bicarbonate and brine, dried, and concentrated in vacuo to provide the title compound. The NMR spectrum, which was consistent with the assigned structure, indicated that the sample still contained $CH_2Cl_2$.

b.
5-Bromo-3-(4-fluorophenyl)-2-(4-methylsulfonylphenyl)thiophene

The material from Example 4a above, combined with material from a 20 mmole reaction carried out in essentially the same manner, was dissolved in methylene chloride (75 ml) and diluted with 75 ml of acetic acid. The reaction mixture was cooled to about 5° and treated with a 1M solution of bromine in acetic acid (24.2 ml, 1.1 equiv). After 3 hours the reaction mixture was concentrated in vacuo. The residue was dissolved in ethyl acetate, washed with saturated aqueous sodium bicarbonate and brine, dried, and concentrated in vacuo. Recrystallization from methanol gave the title compound (5.6 g), m.p. 141°–145°. Infrared and NMR spectral data were consistent with the assigned structure
MS: m/z 410 and 412 (M+).

The compounds of Examples 1, 2, 3 and 4 are listed in Table I.

TABLE I $$R^1 \underset{S}{\overset{R^2}{\diagdown\!\!\!\diagup}} Br$$

| Ex. | $R^1$ | $R^2$ | m.p. (°C.) |
|---|---|---|---|
| 1 | 4-MeSC$_6$H$_4$ | 4-FC$_6$H$_4$ | 113–116 |
| 2 | 4-FC$_6$H$_4$ | 4-MeSO$_2$C$_6$H$_4$ | 122–124 |
| 3 | 4-FC$_6$H$_4$ | 4-MeSC$_6$H$_4$ | 75–78 |
| 4 | 4-MeSO$_2$C$_6$H$_4$ | 4-FC$_6$H$_4$ | 141–145 |

Dosage Forms

The antiinflammatory agents of this invention can be administered to treat inflammation by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose.

Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Use

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973 "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Male Charles River Lewis rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). Twenty non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or 0.25% Methocel ® (methylcellulose: DOW Chemical type A15C, viscosity 1500 cps) (10 ml/kg) by gavage on that day and on the 6 following days. One day after the last dose the paw volumes (uninjected, left hind paw) are measured using a Ugo Basile Volume Differential Meter Model 7101.

$$\frac{\substack{\text{Arthritic Control} \\ \text{Mean Paw Volume (ml)}} - \substack{\text{Treatment Group} \\ \text{Mean Paw Volume (ml)}}}{\substack{\text{Arthritic Control} \\ \text{Mean Paw Volume (ml)}} - \substack{\text{Non-Arthritic Control} \\ \text{Mean Paw Volume (ml)}}} \times 100 =$$

% Decrease from Control Mean Paw Volume.

Dose-response regression lines of the percent decrease are plotted on semi-log paper by visual fit and the ED50% decrease from control paw volume is determined by inspection. Data for the compounds in this invention are summarized in Table II.

Compounds from this series were also compared to indomethacin, phenylbutazone, ibuprofen, and aspirin.

Prostaglandin Synthetase Inhibition Assay

Inhibition of bovine seminal vesicle prostaglandin synthetase (PGS) was measured by the method of White and Glassman [*Prostaglandins*, 7, 123–129 (1974)] as modified by Vigdahl and Tukey [*Biochem. Pharmacol.*, 26, 307–311 (1977)]. $^{14}$C-Arachidonic acid was used as a substrate at a final concentration of 0.02 mM. The resulting labelled prostaglandins were isolated on small columns of Bio-Sil ® A silica gel. The reaction was buffered with 0.13M Tris.Cl (pH 8.5) and included 0.06 mM epinephrine, 2.1 mM reduced glutathione, and 0.09 mM EDTA, which favored $PGE_2$ as the primary product [C. Takeguchi, et al., Biochem., Vol. 10, 2372–2376 (1971)]. Miles bovine seminal vesicle prostaglandin synthetase (20 μg), inhibitor, cofactor, and buffer were mixed and preincubated for two minutes at 37° C. The substrate was added to initiate the reaction which was run for 10 minutes. The reaction was stopped by freezing in a slurry of dry ice/ethanol. All reactions were run in duplicate. Inhibitors were bead-milled overnight and diluted in reaction buffer (0.2M Tris.Cl, pH 8.5). Inhibition was calculated by the following formula:

$$\% \text{ Inhibition} = \left[ 1 - \frac{(DPM \text{ inhibited}) - (DPM \text{ blank})}{(DPM \text{ uninhibited}) - (DPM \text{ blank})} \right] \times 100\%$$

A semilog plot of percent inhibition versus final concentration of inhibitor was used to determine by inspection the concentration that inhibited the reaction by 50% (IC50).

TABLE II

| Example | Adjuvant Arthritis ED$_{50}$ (mg/kg) | PGS IC$_{50}$ (μM) |
| --- | --- | --- |
| 1 | 1.4 | 8 |
| 2 | 0.21 | 24 |
| 3 | 0.25 | 54 |
| 4 | 0.4 | 550 |
| Indomethacin | 0.25 | 3.2 |
| Phenylbutazone | 10 | 270 |
| Ibuprofen | 80 | 95 |
| Aspirin | 290 | 2200 |

What is claimed is:

1. A compound of the formula:

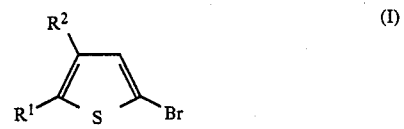

(I)

wherein
R$^1$ is 4-fluorophenyl, 4-methylthiophenyl, or 4-methylsulfonylphenyl; and
R$^2$ is 4-fluorophenyl, 4-methylthiophenyl, or 4-methylsulfonylphenyl;
with the proviso that there must be one, and only one, 4-fluorophenyl substituent selected for R$^1$ and R$^2$.

2. The compound of claim 1 which is 5-bromo-3-(4-fluorophenyl)-2-(4-methylthiophenyl)thiophene.

3. The compound of claim 1 which is 5-bromo-2-(4-fluorophenyl)-3-(4-methylsulfonylphenyl)thiophene.

4. The compound of claim 1 which is 5-bromo-2-(4-fluorophenyl)-3-(4-methylthiophenyl)thiophene.

5. The compound of claim 1 which is 5-bromo-3-(4-fluorophenyl)-2-(4-methylsulfonylphenyl)thiophene.

* * * * *